(12) United States Patent
Kamiya et al.

(10) Patent No.: US 9,534,494 B2
(45) Date of Patent: Jan. 3, 2017

(54) OPTICAL WINDOW ASSEMBLIES

(71) Applicant: Schlumberger Technology Corporation, Sugar Land, TX (US)

(72) Inventors: Akira Kamiya, Sagamihara (JP); Stephane Vannuffelen, Meudon (FR); Kamal Kader, Minato-ku (JP); Hua Chen, Yokohama (JP); Hisatoshi Matsumoto, Machida (JP)

(73) Assignee: Schlumberger Technology Corporation, Sugar Land, TX (US)

( * ) Notice: Subject to any disclaimer, the term of this patent is extended or adjusted under 35 U.S.C. 154(b) by 15 days.

(21) Appl. No.: 13/776,683

(22) Filed: Feb. 25, 2013

(65) Prior Publication Data

US 2014/0240862 A1 Aug. 28, 2014

(51) Int. Cl.
| | |
|---|---|
| *G02B 5/00* | (2006.01) |
| *G02B 7/00* | (2006.01) |
| *E21B 49/10* | (2006.01) |
| *E21B 47/10* | (2012.01) |
| *G01N 21/09* | (2006.01) |
| *G01N 33/28* | (2006.01) |
| *G01N 21/03* | (2006.01) |
| *G01N 21/05* | (2006.01) |

(52) U.S. Cl.
CPC .............. *E21B 49/10* (2013.01); *E21B 47/10* (2013.01); *G01N 21/09* (2013.01); *G01N 21/0317* (2013.01); *G01N 21/05* (2013.01); *G01N 33/2823* (2013.01); *G01N 2021/0389* (2013.01); *G01N 2201/08* (2013.01)

(58) Field of Classification Search
CPC .... G01N 21/05; G01N 21/0303; G01N 21/53; B01L 2300/0877; B01L 2200/0636; G02B 27/0994; G02B 1/06; G02B 6/0006
USPC .................................. 359/894, 895; 356/246
See application file for complete search history.

(56) References Cited

U.S. PATENT DOCUMENTS

| 4,588,893 | A | | 5/1986 | Vidrine et al. | |
|---|---|---|---|---|---|
| 5,078,493 | A | * | 1/1992 | Evens et al. | .................. 356/246 |
| 5,905,271 | A | | 5/1999 | Wynn | |
| 5,949,536 | A | | 9/1999 | Mark | |

(Continued)

FOREIGN PATENT DOCUMENTS

WO 2014/130916 8/2014

OTHER PUBLICATIONS

International search report and written opinion for the equivalent PCT patent application No. PCT/US2014/017893 issued on Jun. 3, 2014.

(Continued)

*Primary Examiner* — Jade R Chwasz
(74) *Attorney, Agent, or Firm* — Daryl R. Wright; Jody Lynn DeStefani

(57) ABSTRACT

Optical window assemblies are provided. An example apparatus includes a first fixture defining a fluid flow passageway. The example apparatus also includes a second fixture defining an aperture. The second fixture is coupled to the first fixture. A first optical window is disposed in the aperture. The first optical window has a first end and a second end. The first end is to be in contact with fluid in the fluid flow passageway, and a cross-sectional size of the first optical window decreases from the first end toward the second end along a portion of the first optical window.

15 Claims, 9 Drawing Sheets

(56) References Cited

U.S. PATENT DOCUMENTS

| | | |
|---|---|---|
| 7,114,562 B2 | 10/2006 | Fisseler et al. |
| 7,336,356 B2 | 2/2008 | Vannuffelen et al. |
| 7,379,180 B2 | 5/2008 | Vannuffelen et al. |
| 2004/0218176 A1 | 11/2004 | Shammal et al. |
| 2008/0252881 A1 | 10/2008 | Yakimoski et al. |
| 2012/0300200 A1 | 11/2012 | Atkinson et al. |
| 2013/0219997 A1 | 8/2013 | Sullivan et al. |

OTHER PUBLICATIONS

Extended European search report for the equivalent European patent application No. 14187107.9 issued on Oct. 21, 2015.

\* cited by examiner

OPTICAL WINDOW ASSEMBLIES

BACKGROUND

In certain applications, formation fluid is extracted from a subterranean formation into a flowline of a downhole tool. As the formation fluid flows through the flowline, the formation fluid may be analyzed to determine one or more characteristics and/or properties of the formation fluid.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

An example apparatus includes a first fixture defining a fluid flow passageway. The example apparatus also includes a second fixture defining an aperture. The second fixture is coupled to the first fixture. A first optical window is disposed in the aperture. The first optical window has a first end and a second end. The first end is to be in contact with fluid in the fluid flow passageway, and a cross-sectional size of the first optical window decreases from the first end toward the second end along a portion of the first optical window.

Another example apparatus includes a first fixture defining a first frustum-shaped space to be in communication with a fluid flow passageway. The example apparatus also includes a first optical window. A portion of the first optical window is frustum-shaped and disposed in the first frustum-shaped space. The example apparatus further includes a second fixture coupled to the first fixture. The second fixture defines the fluid flow passageway.

Another example apparatus includes a first optical window to be in communication with a fluid flow passageway. The first optical window includes a tapered portion. The example apparatus also includes a first fixture defining a space to receive the tapered portion of the first optical window. The first optical window is to be fused to the first fixture. The first fixture is coupled to a second fixture, which defines the fluid flow passageway.

Figure 1:
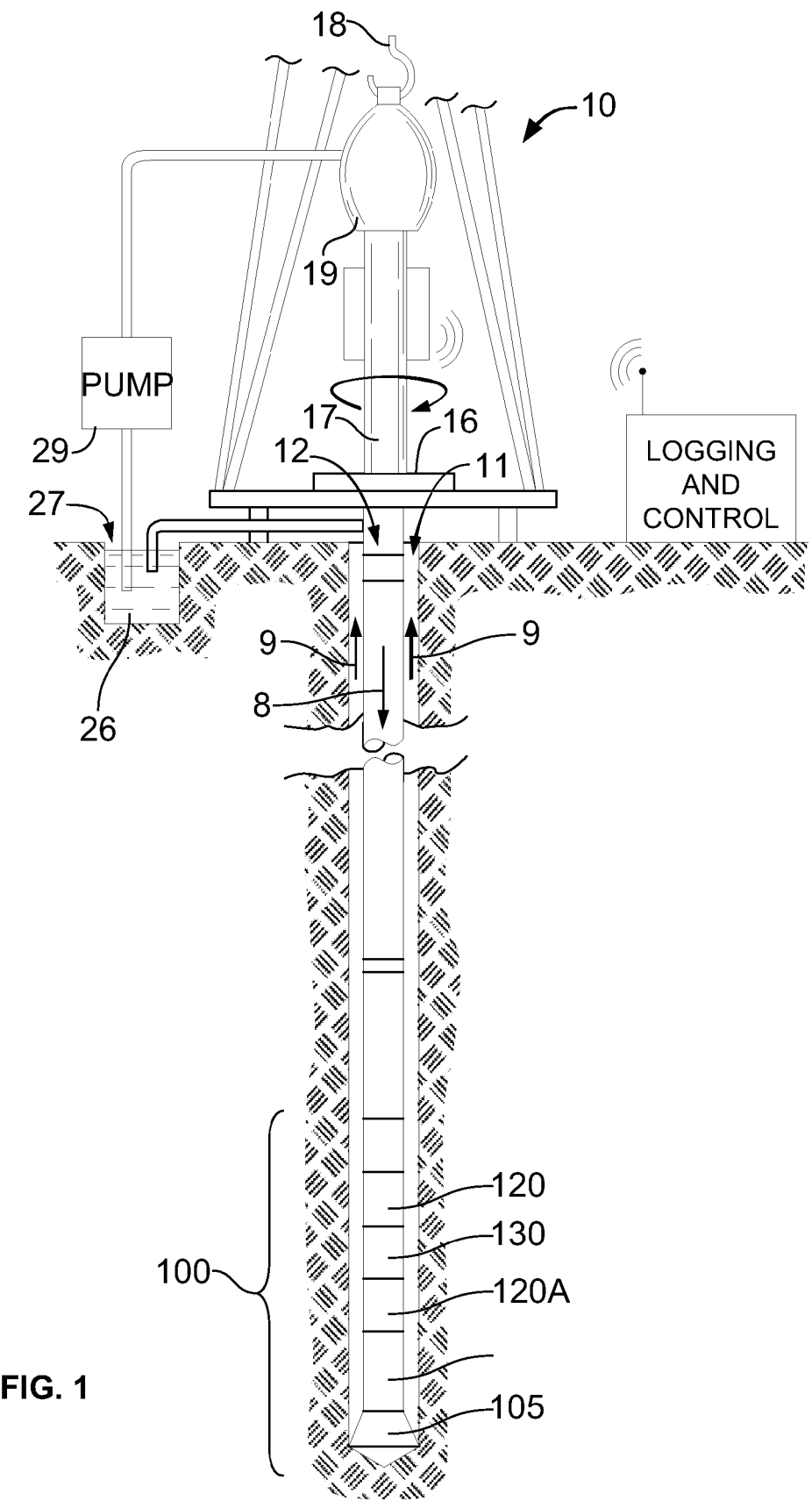
FIG. 1 illustrates an example system in which embodiments of optical window assemblies can be implemented.

The figures are not to scale. Instead, to clarify multiple layers and regions, the thickness of the layers may be enlarged in the drawings. Wherever possible, the same reference numbers will be used throughout the drawing(s) and accompanying written description to refer to the same or like parts. As used in this patent, stating that any part (e.g., a layer, film, area, or plate) is in any way positioned on (e.g., positioned on, located on, disposed on, or formed on, etc.) another part, means that the referenced part is either in contact with the other part, or that the referenced part is above the other part with one or more intermediate part(s) located therebetween. Stating that any part is in contact with another part means that there is no intermediate part between the two parts.

DETAILED DESCRIPTION

FIG. 1 illustrates a wellsite system in which examples disclosed herein can be employed. The wellsite can be onshore or offshore. In this example system, a borehole 11 is formed in subsurface formations by rotary drilling in a manner that is well known. Other examples can also use directional drilling, as will be described hereinafter.

A drill string 12 is suspended within the borehole 11 and has a bottom hole assembly 100 which includes a drill bit 105 at its lower end. The surface system includes platform and derrick assembly 10 positioned over the borehole 11, the derrick assembly 10 including a rotary table 16, a kelly 17, a hook 18 and a rotary swivel 19. The drill string 12 is rotated by the rotary table 16, energized by means not shown, which engages the kelly 17 at an upper end of the drill string 12. The drill string 12 is suspended from the hook 18, attached to a traveling block (also not shown), through the kelly 17 and the rotary swivel 19, which permits rotation of the drill string 12 relative to the hook 18. In some examples, a top drive system could be used.

In the illustrated example, the surface system further includes drilling fluid or mud 26 stored in a pit 27 formed at the well site. A pump 29 delivers the drilling fluid 26 to the interior of the drill string 12 via a port in the swivel 19, causing the drilling fluid 26 to flow downwardly through the drill string 12 as indicated by directional arrow 8. The drilling fluid 26 exits the drill string 12 via ports in the drill bit 105, and then circulates upwardly through the annulus region between the outside of the drill string 12 and the wall of the borehole 11, as indicated by directional arrows 9. In this manner, the drilling fluid 26 lubricates the drill bit 105 and carries formation cuttings up to the surface as it is returned to the pit 27 for recirculation.

The bottom hole assembly 100 of the illustrated example includes a logging-while-drilling (LWD) module 120, a measuring-while-drilling (MWD) module 130, a roto-steerable system and motor, and the drill bit 105.

The LWD module 120 is housed in a special type of drill collar, as is known in the art, and can contain one or more logging tools. It will also be understood that more than one LWD and/or MWD module can be employed, for example, as represented at 120A. References throughout to a module at the position of module 120 can mean a module at the position of module 120A. The LWD module 120 includes capabilities for measuring, processing, and storing informa-tion, as well as for communicating with the surface equipment. In the illustrated example, the LWD module 120 includes a fluid sampling device.

The MWD module 130 is also housed in a special type of drill collar, as is known in the art, and can contain one or more devices for measuring characteristics of the drill string 12 and the drill bit 105. The MWD module 130 further includes an apparatus (not shown) for generating electrical power to the downhole system. This may include a mud turbine generator powered by the flow of the drilling fluid 26, and/or other power and/or battery systems. In the illustrated example, the MWD module 130 includes one or more of the following types of measuring devices: a weight-on-bit measuring device, a torque measuring device, a vibration measuring device, a shock measuring device, a stick slip measuring device, a direction measuring device, and an inclination measuring device.

Figure 2:
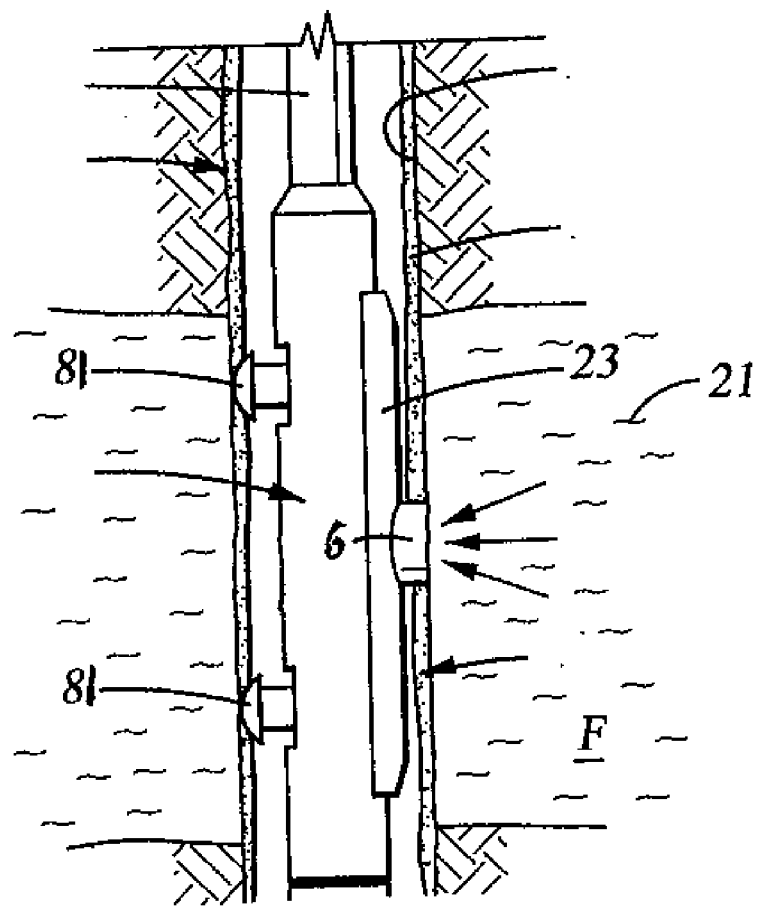
FIG. 2 illustrates another example system in which embodiments of optical window assemblies can be implemented.

FIG. 2 is a simplified diagram of a sampling-while-drilling logging device of a type described in U.S. Pat. No. 7,114,562, incorporated herein by reference, utilized as the LWD tool 120 or part of the LWD tool suite 120A. The LWD tool 120 is provided with a probe 6 for establishing fluid communication with the formation and drawing fluid 21 into the tool 120, as indicated by the arrows. The probe 6 may be positioned in a stabilizer blade 23 of the LWD tool 120 and extended therefrom to engage a borehole wall. The stabilizer blade 23 comprises one or more blades that are in contact with the borehole wall. The fluid 21 drawn into the tool 120 using the probe 6 may be measured to determine, for example, pretest and/or pressure parameters and/or properties and/or characteristics of the fluid 21 such as, for example, optical densities. The LWD tool 120 may be provided with devices, such as sample chambers, for collecting fluid samples for retrieval at the surface. Backup pistons 81 may also be provided to assist in applying force to push the drilling tool and/or probe 6 against the borehole wall.

Figure 3:
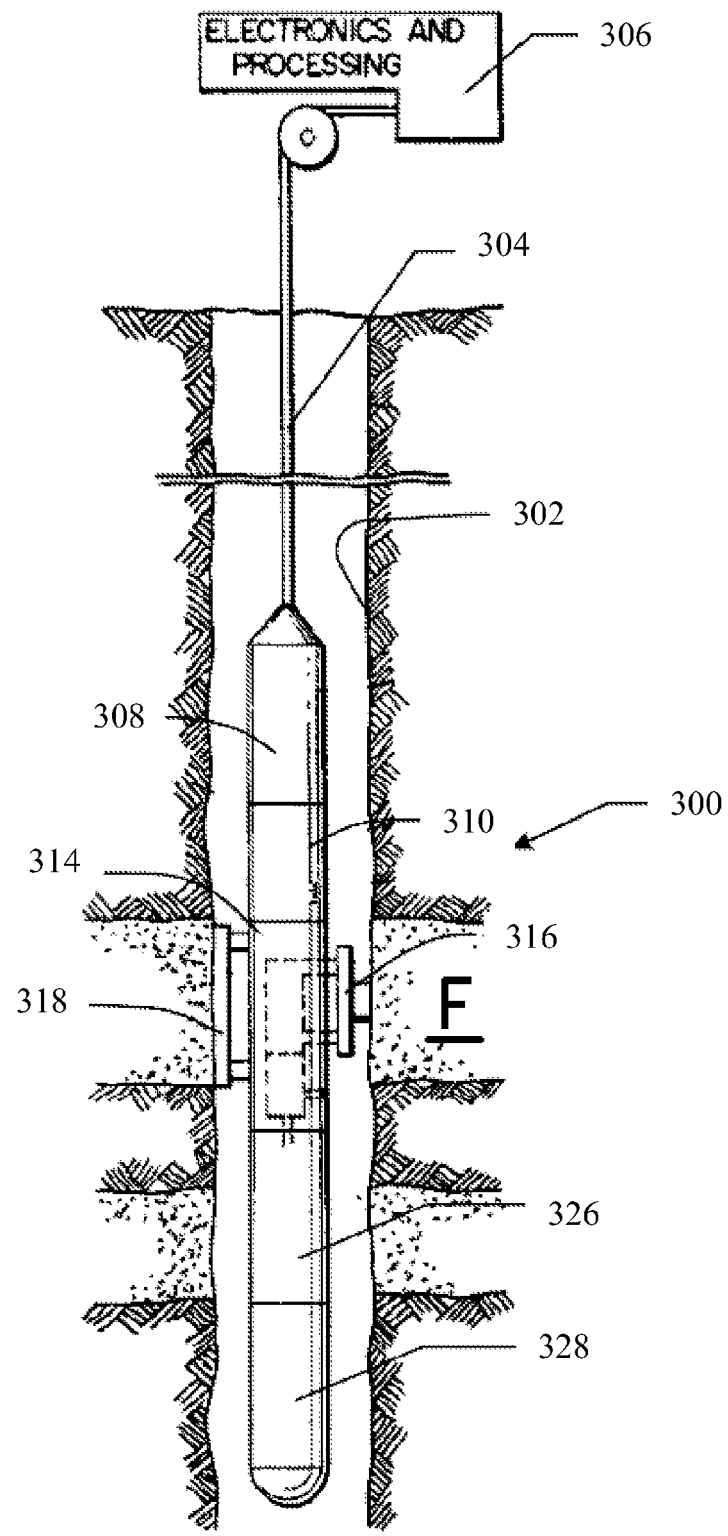
FIG. 3 illustrates another example system in which embodiments of optical window assemblies can be implemented.

FIG. 3 illustrates an example wireline tool 300 that may be another environment in which aspects of the present disclosure may be implemented. The example wireline tool 300 is suspended in a wellbore 302 from a lower end of a multiconductor cable 304 that is spooled on a winch (not shown) at the Earth's surface. At the surface, the cable 304 is communicatively coupled to an electronics and processing system 306. The example wireline tool 300 includes an elongated body 308 that includes a formation tester 314 having a selectively extendable probe assembly 316 and a selectively extendable tool anchoring member 318 that are arranged on opposite sides of the elongated body 308. Additional components (e.g., 310) may also be included in the tool 300.

One or more aspects of the probe assembly 316 may be substantially similar to those described above in reference to the probe 6 of FIG. 2. For example, the extendable probe assembly 316 is configured to selectively seal off or isolate selected portions of the wall of the wellbore 302 to fluidly couple to an adjacent formation F and/or to draw fluid samples from the formation F. Accordingly, the extendable probe assembly 316 may be provided with a probe having an embedded plate. The formation fluid may be expelled through a port (not shown) or it may be sent to one or more fluid collecting chambers 326 and 328. In the illustrated example, the electronics and processing system 306 and/or a downhole control system are configured to control the extendable probe assembly 316 and/or the drawing of a fluid sample from the formation F.

Figure 4:
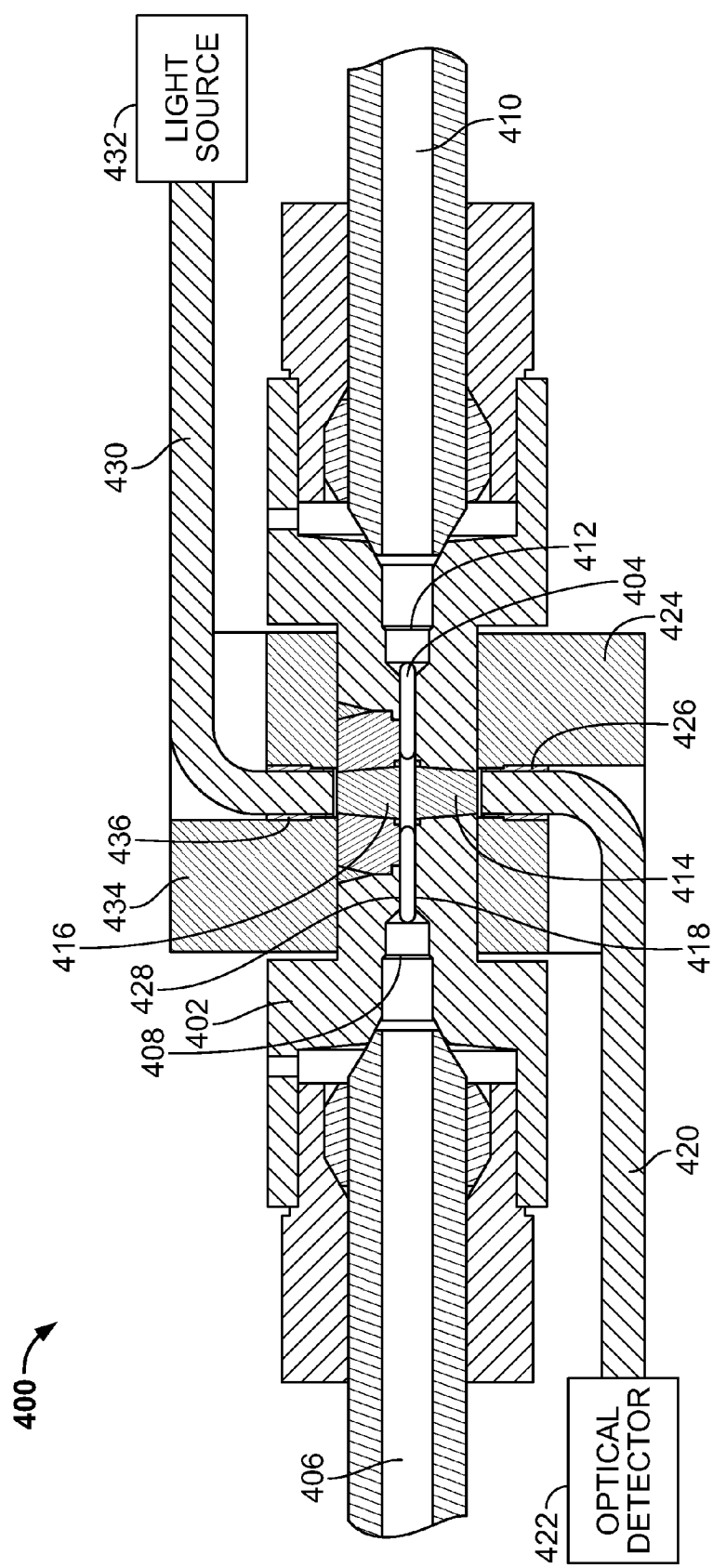
FIG. 4 illustrates an example optical window assembly disclosed herein.

FIG. 4 illustrates an example optical window assembly 400 disclosed herein, which may be used to analyze formation fluid flowing in a downhole tool such as, for example, the LWD tool 120 of FIGS. 1-2, the wireline tool 300, and/or any other suitable downhole tool. The example optical window assembly 400 may be used in a variety of downhole applications such as, for example, logging-while-drilling, sampling, production logging, etc. In the illustrated example, the optical window assembly 400 includes a first fixture 402. In some examples, the first fixture 402 is coupled to and/or integral with a chassis of the downhole tool (e.g., a support disposed in the drill string 100). The example first fixture 402 defines a fluid flow passageway 404 in fluid communication with a subterranean formation via a first flowline 406. In the illustrated example, the first flowline 406 is coupled to the first fixture 402 via a first connector or fitting 408. The example fluid flow passageway 404 is also in fluid communication with a second flowline 410. In the illustrated example, the second flowline 410 is coupled to the first fixture 402 via a second connector or fitting 412. The second flowline 410 may direct fluid to a port (not shown) through which the fluid is expelled (e.g., into the borehole 11). In some examples, the second flowline 410 directs the fluid to one or more fluid collecting chambers (e.g., the fluid collecting chambers 326 and 328 of FIG. 3). In some examples, one or more sensors, valves, gauges, flowlines and/or other devices are disposed along the first flowline 406 and/or the second flowline 410 to direct and/or control fluid flow and/or determine one or more characteristics and/or properties of the fluid.

A first optical window 414 and a second optical window 416 are in optical communication via the fluid flow passageway 404. In the illustrated example, the first optical window 414 is disposed on a first side 418 of the fluid flow passageway 404. A first fiber bundle 420 is operatively coupled to a photodetector or optical detector 422 (e.g., a spectrometer) and the first optical window 414 to define an optical path between the optical detector 422 and the first optical window 414. A fiber bundle is a cable including one or more optical fibers to define an optical path. Other examples may employ different and/or additional devices to define the optical path and/or direct light from the first optical window 414 to the optical detector 422 such as, for example, one or more optics (e.g., lenses, filters, mirrors, etc.). In the illustrated example, the first fiber bundle 420 is directed to the first optical window 414 via a first cap 424. The example first cap 424 defines a first channel 426 to direct the first fiber bundle 420 to the first optical window 414. The first cap 424 may be coupled to the first fixture 402 via, for example, a brazed connection, a weld, an adhesive, etc. In some examples, the first cap 424 is removably coupled to the first fixture 402 via, for example, mechanical fasteners (e.g., bolts) to enable disassembly and/or reassembly of the first cap 424 with the optical window assembly 400 to facilitate maintenance and/or cleaning of the first fiber bundle 420, the first optical window 414, and/or other components of the optical window assembly 400.

The example second optical window 416 is disposed on a second side 428 of the fluid flow passageway 404 opposite the first side 418. Thus, the fluid flow passageway 404 interposes the first optical window 414 and the second optical window 416. A second fiber bundle 430 is optically coupled to light source 432 (e.g., one or more diode lasers, light emitting diodes (LEDs), etc.) and the second optical window 416 to define an optical path between the light source 432 and the second optical window 416. Other examples may employ different and/or additional devices to define the optical path and/or direct light from the light source 432 to the second optical window 416 such as, for example, one or more optics (e.g., lenses, filters, mirrors, etc.). In the illustrated example, the second fiber bundle 430 is directed to the second optical window 416 via a second cap 434. The example second cap 434 directs the second fiber bundle 430 to the second optical window 416 via a second channel 436. The example second cap 434 may be coupled to the first fixture 402 via, for example, a brazed connection, a weld, an adhesive, etc. In some examples, the second cap 434 is removably coupled to the first fixture 402 via, for example, mechanical fasteners (e.g., bolts) to enable disassembly and/or reassembly of the second cap 434 with the optical window assembly 400 to facilitate maintenance and/or cleaning of the second fiber bundle 430, the second optical window 416, and/or other components of the example optical window assembly 400.

The example optical window assembly 400 of FIG. 4 may be used to determine one or more characteristics and/or properties of the fluid flowing through the fluid flow passageway 404. For example, during a downhole operation, the fluid is extracted from a subterranean formation and flowed into the downhole tool (e.g., via the probe 6, the probe assembly 316, etc.). The fluid flows into the first flowline 406 to the fluid flow passageway 404. The light source 432 is operated to interact light with the fluid flowing through the fluid flow passageway 404. For example, the light emitted from the light source 432 passes through the second fiber bundle 430 and the second optical window 416 into the fluid flow passageway 404, where the light interacts with the fluid. When the light interacts with the fluid, some of the light may be absorbed, reflected, scattered etc. by the fluid, and some of the light may pass through the fluid and into the first optical window 414. In the illustrated example, the light passing through the fluid is directed from the first optical window 414 to the optical detector 422 via the first fiber bundle 420. Light received by the optical detector 422 may be analyzed (e.g., by detecting and/or measuring optical densities) to determine one or more characteristics and/or properties of the fluid.

Figure 5:
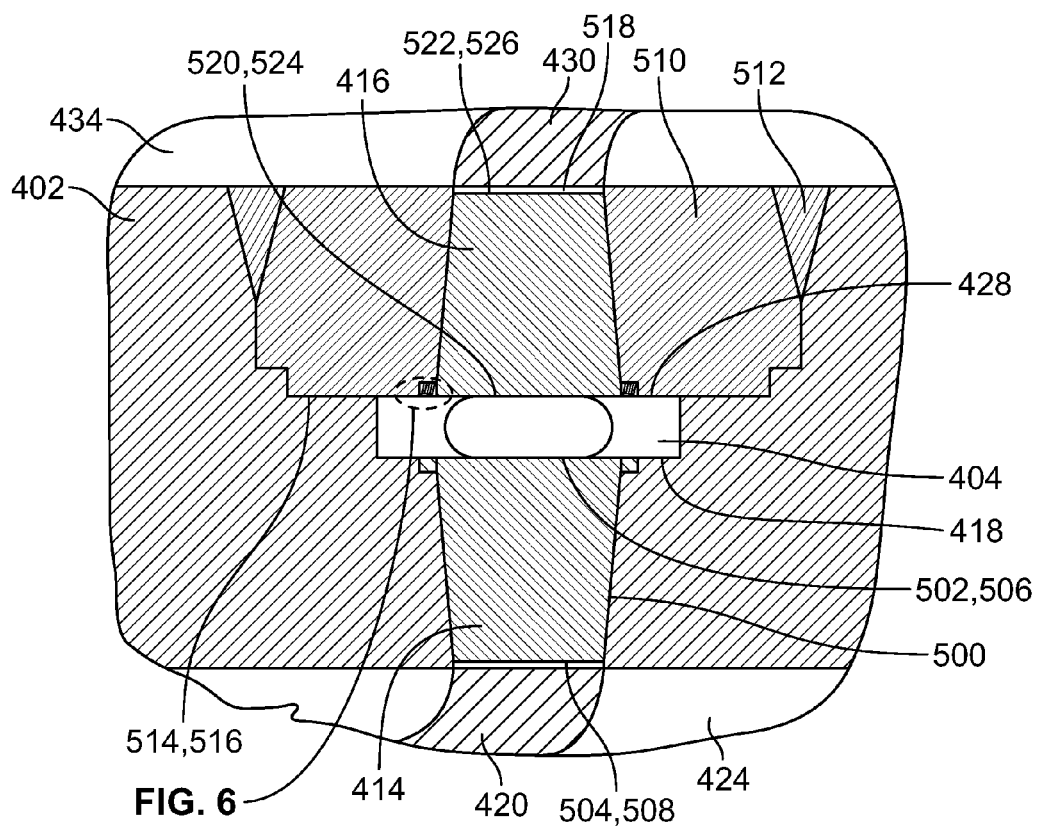
FIG. 5 illustrates a first optical window and a second optical window of the example optical window assembly of FIG. 4.

FIG. 5 is an enlarged view of the first optical window 414 and the second optical window 416. The example first fixture 402 of FIG. 5 defines a first space or aperture 500 in communication with the fluid flow passageway 404 to receive the first optical window 414. In the illustrated example, the first aperture 500 has a tapered shape (e.g., frustum-shaped, cone-shaped, etc.) such that a first portion 502 of the first aperture 500 adjacent the fluid flow passageway 404 has a first cross-sectional size (e.g., diameter, area, etc.) and a second portion 504 of the first aperture 500 adjacent the first fiber bundle 420 has a second cross-sectional size (e.g., diameter, area, etc.) less than the first size.

The example first optical window 414 is disposed in the first aperture 500. A first end 506 of the first optical window 414 is adjacent the fluid flow passageway 404. As the fluid flows through the fluid flow passageway 404, the fluid flows across and contacts the first end 506 of the first optical window 414. A second end 508 of the first optical window 414 is operatively coupled to the first fiber bundle 420. In the illustrated example, the first optical window 414 has a tapered shape (e.g., frustum-shaped, cone-shaped, etc.). The tapered shape is such that a cross-sectional size of the first optical window 414 decreases from the first end 506 toward the second end 508 along at least a portion of the first optical window 414. In the illustrated example, the first optical window 414 is substantially composed of sapphire ($Al_2O_3$). Other examples may be composed of sapphire and/or one or more other materials.

A pressure of the fluid flowing through the fluid flow passageway 404 may be high (e.g., 30,000 pounds per square inch). The tapered shapes of the first optical window 414 and the first aperture 500 enable force applied to the first optical window 414 via the fluid to be transferred to the first fixture 402. As a result, the force from the fluid is substantially not transferred to the first cap 424 and/or the first fiber bundle 420 via the first optical window 414. Thus, the first cap 424 and the first fiber bundle 420 experience substantially no force associated with the pressure of the fluid.

In the illustrated example, the second optical window 416 is coupled to the first fixture 402 via a second fixture 510. The example second fixture 510 is rigidly coupled to the first fixture 402. Rigidly coupling the second fixture 510 to the first fixture 402 involves coupling the second fixture 510 to the first fixture 402 to substantially prevent movement of the second fixture 510 relative to the first fixture 402 during operation of the example optical window assembly 400. In the illustrated example, the second fixture 510 is rigidly coupled to the first fixture 402 via a weld 512 (e.g., an electron beam weld). The weld 512 holds a surface 514 of the second fixture 510 against a surface 516 of the first fixture 402 and forms a fluid seal between the first fixture 402 and the second fixture 510 (e.g., between the surfaces 514, 516 and/or at the weld 512 about a perimeter of the second fixture 510, etc.). In other examples, the first fixture 402 may be rigidly coupled to the second fixture 510 via other techniques such as, for example, mechanical fasteners (e.g., one or more bolts, screws, etc.), a brazed connection, an adhesive, etc. In the illustrated example, no pliable seals (e.g., rubber o-rings) that would enable the first fixture 402 to float or move relative to the second fixture 510 are employed to provide the fluid seal between the first fixture 402 and the second fixture 510. Rather, the example second fixture 510 is fused to the first fixture 402 via the weld 512 to provide the fluid seal and hold the second fixture 510 in place relative to the first fixture 402.

The example second fixture 510 of FIG. 5 defines a second space or aperture 518 in communication with the fluid flow passageway 404 to receive the second optical window 416. In the illustrated example, the second aperture 518 has a tapered shape (e.g., frustum-shaped, cone-shaped, etc.) such that a first portion 520 of the second aperture 518 adjacent the fluid flow passageway 404 has a first size (e.g., diameter, area, etc.) and a second portion 522 of the second aperture 518 adjacent the second fiber bundle 430 has a second size (e.g., diameter, area, etc.) less than the first size. The example second optical window 416 is disposed in the second aperture 518 to enable a first end 524 of the second optical window 416 to be in contact with the fluid as the fluid flows through the fluid flow passageway 404. The second fiber bundle 430 is operatively coupled to a second end 526 of the second optical window 518. In the illustrated example, the second optical window 416 has a tapered shape (e.g., frustum-shaped, cone-shaped, etc.). The tapered shape is such that a cross-sectional size of the second optical window 416 decreases from the first end 524 toward the second end 526 along at least a portion of the second optical window 416. In the illustrated example, the second optical window 416 is substantially composed of sapphire ($Al_2O_3$). In other examples, the second optical window 416 may be composed of sapphire and/or one or more other materials.

The tapered shapes of the second optical window 416 and the second aperture 518 enable force applied to the second optical window 416 via the fluid to be transferred to the second fixture 510 and the first fixture 402. As a result, the force from the fluid is substantially not transferred to the second cap 434 and/or the second fiber bundle 430 via the second optical window 416. Thus, the second cap 434 and the second fiber bundle 430 experience substantially no force associated with fluid pressure in the fluid flow passageway 404.

Figure 6:
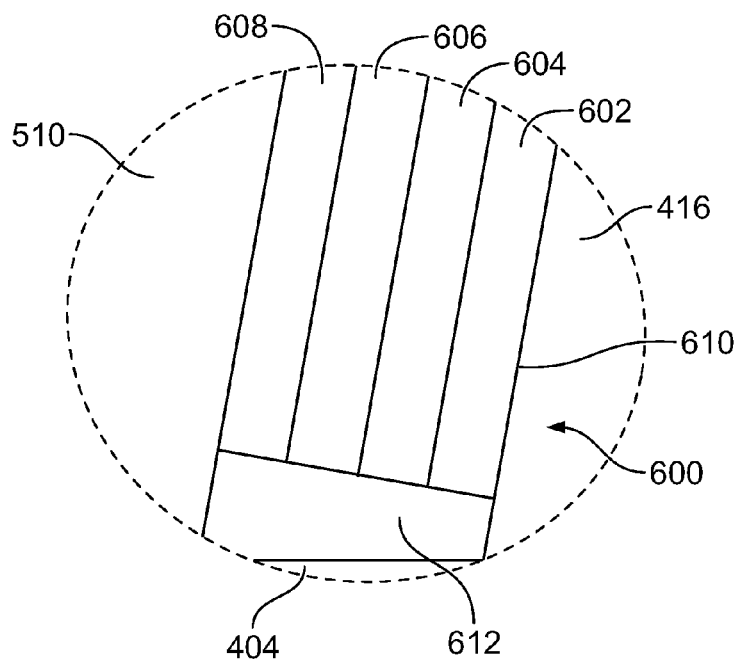
FIG. 6 illustrates an example connection between the second optical window and a first fixture of the optical window assembly of FIGS. 4-5.

FIG. 6 is an enlarged view an example connection 600 between the second optical window 416 and the second fixture 510. In the illustrated example, the connection 600 is a brazed connection to rigidly couple the second optical window 416 to the second fixture 510. The example connection 600 of FIG. 6 is formed by brazing the second optical window 416 to the second fixture 510 via a plurality of brazing layers 602, 604, 606 and 608. Thus, the second optical window 416 is fused to the second fixture 510 via the brazing layers 602, 604, 606 and 608. The connection 600 substantially fills a portion of the second aperture 518 between the second optical window 416 and the second fixture 510 to form a fluid seal between the second optical window 416 and the second fixture 510. In the illustrated example, the first brazing layer 602 includes titanium, which is fused to sides 610 (e.g., a circumferential surface) of the second optical window 416. A second brazing 604 layer of the example connection 600 includes nickel plating. A third brazing layer 606 of the example connection 600 includes brazing material (e.g., one or more reactants, filler materials, etc.). A fourth brazing layer 608 of the example connection 600 includes nickel plating. In the illustrated example, at least a portion of the example second fixture 510 that defines the second aperture 518 is composed of one or more metals such as, for example, titanium, Inconel™, etc. The above-noted materials and number of brazing layers are merely examples. Thus, other materials and/or number of brazing layers may be used without departing from the scope of this disclosure.

In some examples, the fluid flowing through the fluid flow passageway 404 may be potentially harmful or damaging (e.g., corrosive) to a portion of the connection 600 (e.g., the brazing layers 602, 604, 606 and 608). In the illustrated example, the connection 600 includes a shield 612 interposing the brazing layers 602, 604, 606 and 608 and the fluid flow passageway 404 to isolate the brazing layers 602, 604, 606 and 608 from the fluid to prevent the fluid from damaging (e.g., corroding) the brazing layers 602, 604, 606 and 608. For example, the shield 612 is coupled to the brazing layers 602, 604, 606 and 608, the second optical window 416 and the second fixture 510 to form a fluid seal against the second optical window 416 and the second fixture 510 to prevent the fluid from contacting the brazing layers 602, 604, 606 and 608. The shield 612 may be a polyetheretherketone (PEEK) molding, a diamond-like carbon (DLC) coating, and/or any other suitable shield.

The first optical window 414 is rigidly coupled to the first fixture 402 via a connection substantially similar or identical to the example connection 600 of FIG. 6. Thus, to avoid redundancy, the connection between the first optical window 414 and the first fixture 402 is not separately described herein. The first optical window 414 and second optical window 416 are substantially held in place relative to the fluid flow passageway 404. As a result, the optical path length between the first optical window 414 and the second optical window 416 (e.g., a distance between the first end 506 of the first optical window 414 and the first end 524 of the second optical window 416) is substantially constant during operation of the example optical window assembly 400. In the illustrated example, the optical path length is about two millimeters. However, the above-noted optical path length is merely an example and, thus, other examples may employ other optical path lengths without departing from the scope of this disclosure. Further, an optical alignment between the first optical window 414 and the second optical window 416 (e.g., an orientation of a longitudinal axis of the first optical window 414 relative to a longitudinal axis of the second optical window 416) is substantially constant during operation.

Figure 7:
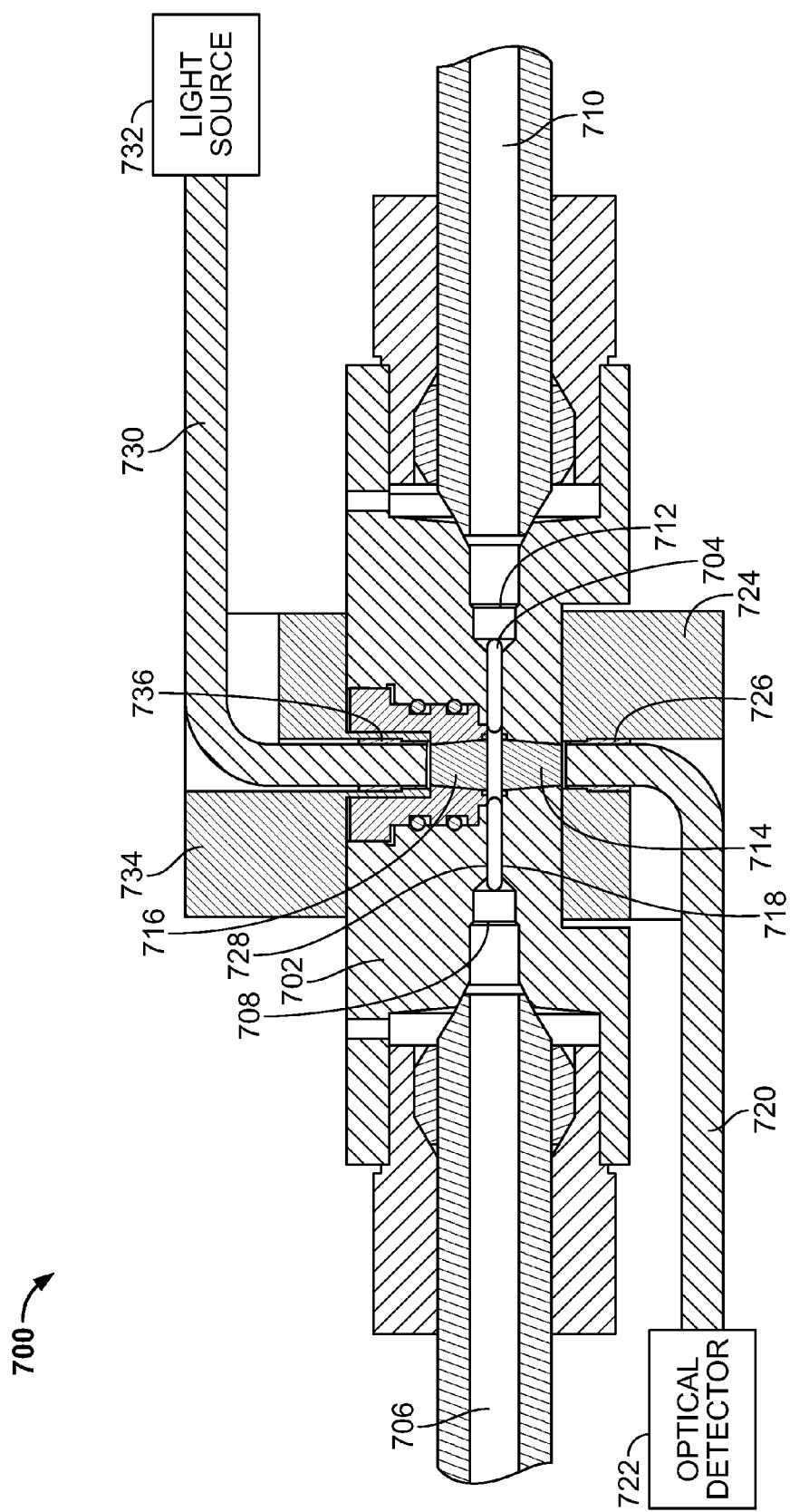
FIG. 7 illustrates another example optical window assembly disclosed herein.

FIG. 7 illustrates another example optical window assembly 700 disclosed herein, which may be used to analyze formation fluid flowing in a downhole tool such as, for example, the LWD tool 120 of FIGS. 1-2, the wireline tool 300, and/or any other suitable downhole tool. The example optical window assembly 400 may be used in a variety of downhole applications such as, for example, logging-while-drilling, sampling, production logging, etc. In the illustrated example, the optical window assembly 700 includes a first fixture 702. In some examples, the first fixture 702 is coupled to and/or integral with a chassis of the downhole tool (e.g., a support disposed in the drill string 100). The example first fixture 702 defines a fluid flow passageway 704 in fluid communication with a subterranean formation via a first flowline 706. In the illustrated example, the first flowline 706 is coupled to the first fixture 702 via a first connector or fitting 708. The example fluid flow passageway 704 is also in fluid communication with a second flowline 710. In the illustrated example, the second flowline 710 is coupled to the first fixture 702 via a second connector or fitting 712. The second flowline 710 may direct fluid from the fluid flow passageway 704 to a port (not shown) through which the fluid is expelled (e.g., into the borehole 11). In some examples, the second flowline 710 directs the fluid to one or more fluid collecting chambers (e.g., the fluid collecting chambers 326 and 328 of FIG. 3). In some examples, one or more sensors, valves, gauges, flowlines and/or other devices are in fluid communication with the first flowline 706 and/or the second flowline 710 to direct and/or control fluid flow and/or determine one or more characteristics and/or properties of the fluid.

A first optical window 714 and a second optical window 716 are in optical communication via the fluid flow passageway 704. In the illustrated example, the first optical window 714 is disposed on a first side 718 of the fluid flow passageway 704. A first fiber bundle 720 is operatively coupled to a photodetector or optical detector 722 (e.g., a spectrometer) and the first optical window 714 to define an optical path between the optical detector 722 and the first optical window 714. Other examples may employ different and/or additional devices to define the optical path and/or direct light from the first optical window 714 to the optical detector 722 such as, for example, one or more optics (e.g., lenses, filters, mirrors, etc.). In the illustrated example, the first fiber bundle 720 is directed to the first optical window 714 via a first cap 724. The example first cap 724 defines a first channel 726 to direct the first fiber bundle 720 to the first optical window 714. The first cap 724 may be coupled to the first fixture 702 via, for example, a brazed connection, a weld, an adhesive, etc. In some examples, the first cap 724 is removably coupled to the first fixture 702 via, for example, mechanical fasteners (e.g., bolts) to enable disassembly and/or reassembly of the first cap 724 with the optical window assembly 700 to facilitate maintenance and/or cleaning of the first fiber bundle 720, the first optical window 714, and/or other components of the optical window assembly 700.

The example second optical window 716 is disposed on a second side 728 of the fluid flow passageway 704 opposite the first side 718. Thus, the fluid flow passageway 704 interposes the first optical window 714 and the second optical window 716. A second fiber bundle 730 is optically coupled to light source 732 (e.g., one or more diode lasers, light emitting diodes (LEDs), etc.) and the second optical window 716 to define an optical path between the light source 732 and the second optical window 716. Other examples may employ different and/or additional devices to define the optical path and/or direct light from the light source 732 to the second optical window 716 such as, for example, one or more optics (e.g., lenses, filters, mirrors, etc.). In the illustrated example, the second fiber bundle 730 is directed to the second optical window 716 via a second cap 734. The example second cap 734 directs the second fiber bundle 730 to the second optical window 716 via a second channel 736. In some examples, the second cap 734 is removably coupled to the first fixture 702 via, for example, mechanical fasteners (e.g., bolts) to enable disassembly and/or reassembly of the second cap 734 with the optical window assembly 700 to facilitate maintenance and/or cleaning of the second fiber bundle 730, the second optical window 716, and/or other components of the example optical window assembly 700.

Figure 8:
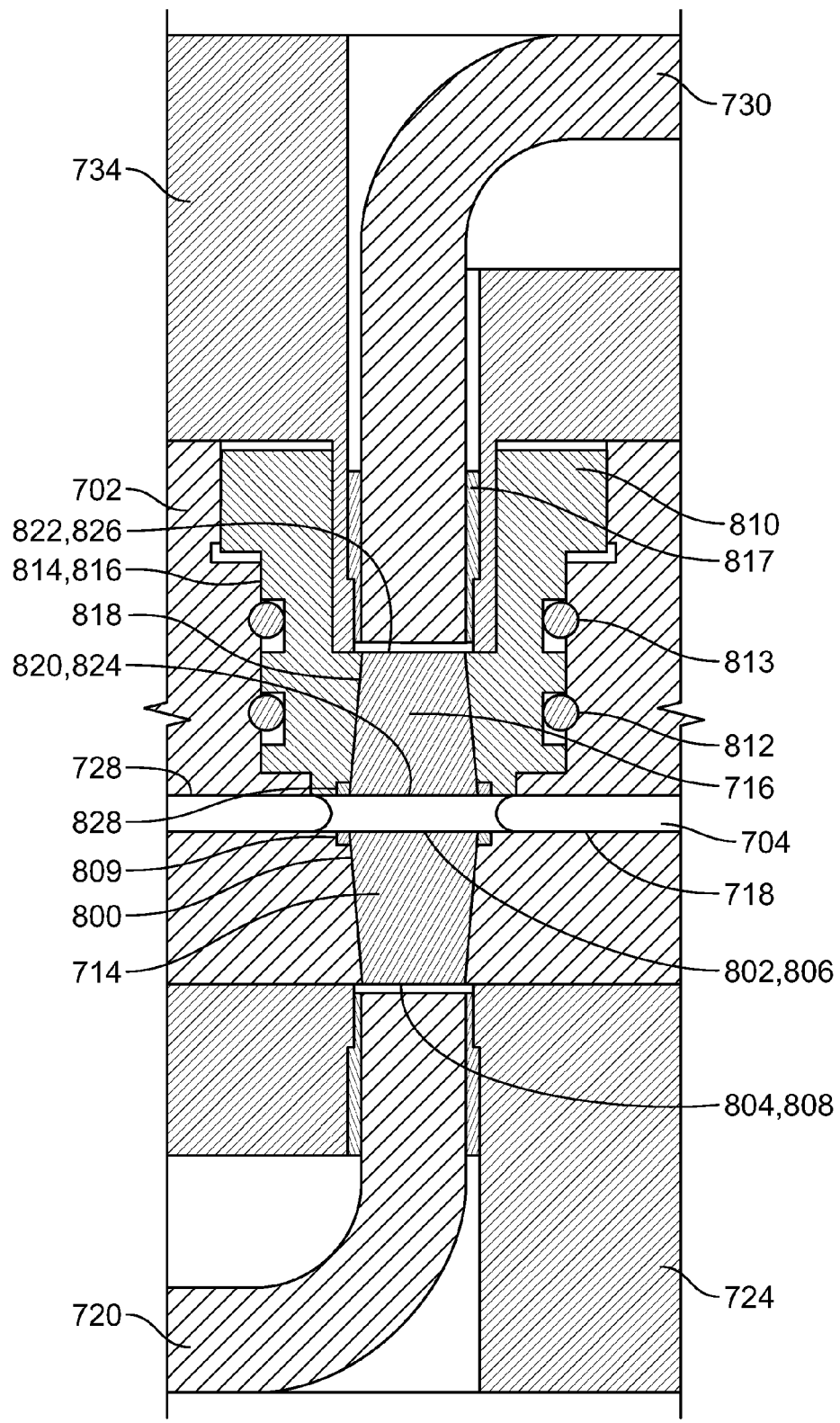
FIG. 8 illustrates a first optical window and a second optical window of the example optical window assembly of FIG. 7.

FIG. 8 is an enlarged view of the first optical window 714 and the second optical window 716. The example first fixture 702 of FIG. 8 defines a first space or aperture 800 in communication with the fluid flow passageway 704 to receive the first optical window 714. In the illustrated example, the first aperture 800 has a tapered shape (e.g., frustum-shaped, cone-shaped, etc.) such that a first portion 802 of the first aperture 800 adjacent the fluid flow passageway 704 has a first size (e.g., diameter, area, etc.) and a second portion 804 of the first aperture 800 adjacent the first fiber bundle 720 has a second size (e.g., diameter, area, etc.) less than the first size.

The example first optical window 714 is disposed in the first aperture 800. A first end 806 of the first optical window 714 is adjacent the fluid flow passageway 704. As the fluid flows through the fluid flow passageway 704, the fluid flows across and contacts the first end 806 of the first optical window 714. A second end 808 of the first optical window 714 is operatively coupled to the first fiber bundle 720. In the illustrated example, the first optical window 714 has a tapered shape (e.g., frustum-shaped, cone-shaped, etc.). The tapered shape is such that a cross-sectional size of the first optical window 714 decreases from the first end 806 toward the second end 808 along at least a portion of the first optical window 714. In the illustrated example, the first optical window 714 is substantially composed of sapphire ($Al_2O_3$). Other examples may be composed of sapphire and/or one or more other materials. The example first optical window 714 is rigidly coupled to the first fixture 702 via a first connection 809. The example first connection 809 provides a fluid seal between the first optical window 714 and the first fixture 702. The first connection 809 may be a brazed connection similar or substantially identical to the example connection 600 of FIG. 6.

A pressure of the fluid flowing through the fluid flow passageway 704 may be high (e.g., 30,000 pounds per square inch). The tapered shapes of the first optical window 714 and the first aperture 800 enable force applied to the first optical window 714 via the fluid to be transferred to the first fixture 702. As a result, the force from the fluid is substantially not transferred to the first cap 724 and/or the first fiber bundle 720 via the first optical window 714. Thus, the first cap 724 and the first fiber bundle 720 experience substantially no force associated with the pressure of the fluid.

In the illustrated example, the second optical window 716 is coupled to the first fixture 702 via a second fixture 810. The example second fixture 810 is removably coupled to the first fixture 702. In some examples, the second fixture 810 is removably coupled to the first fixture 702 via one or more fasteners (e.g., bolts) and/or any other suitable technique. In some examples, the second fixture 810 is also removably coupled to the second cap 734. A first seal 812 (e.g., an o-ring) and a second seal 813 (e.g., an o-ring) are disposed between the first fixture 702 and the second fixture 810 to provide a fluid seal between a surface 814 of the second fixture 810 and a surface 816 of the first fixture 702. The example second fixture 810 defines a third channel 817 to direct the second fiber bundle 730 to the second optical window 716.

The example second fixture 810 of FIG. 8 defines a second space or aperture 818 in communication with the fluid flow passageway 704 and the third channel 817 to receive the second optical window 716. The second aperture 818 has a tapered shape (e.g., frustum-shaped, cone-shaped, etc.) such that a first portion 820 of the second aperture 818 adjacent the fluid flow passageway 704 has a first size (e.g., diameter, area, etc.) and a second portion 822 of the second aperture 818 adjacent the second fiber bundle 730 has a second size (e.g., diameter, area, etc.) less than the first size.

The example second optical window 716 is disposed in the second aperture 818 to enable a first end 824 of the second optical window 716 to be in contact with the fluid as the fluid flows through the fluid flow passageway 704. The second fiber bundle 730 is operatively coupled to a second end 826 of the second optical window 716. In the illustrated example, the second optical window 716 has a tapered shape (e.g., frustum-shaped, cone-shaped, etc.) such that a cross-sectional size of the second optical window 716 decreases from the first end 824 toward the second end 826 along at least a portion of the second optical window 716. In the illustrated example, the second optical window 716 is substantially composed of sapphire ($Al_2O_3$). The second optical window 716 is rigidly coupled to the second fixture 810 via a second connection 828. The example second connection 828 provides a fluid seal between the second optical window 716 and the second fixture 810. The second connection 828 of FIG. 8 may be a brazed connection similar or substantially identical to the example connection 600 of FIG. 6.

The example second fixture 810 may be disassembled from the example first fixture 702, the second fiber bundle 730 and/or the second cap 734 to facilitate maintenance and/or cleaning of the example second optical window 716, the fluid flow passageway 704, the second fiber bundle 730, the second cap 734, and/or other components of the optical window assembly 700. For example, the second fixture 810 may be disassembled from the first fixture 702, the second cap 734 and the second fiber bundle 730 to enable the first end 824 and the second end 826 of the second optical window 716 to be cleaned. When the second fixture 810 is disassembled from the first fixture 702, the first end 806 of the first optical window 714 is accessible via the fluid flow passageway 704 for maintenance, cleaning, etc.

Figure 9:
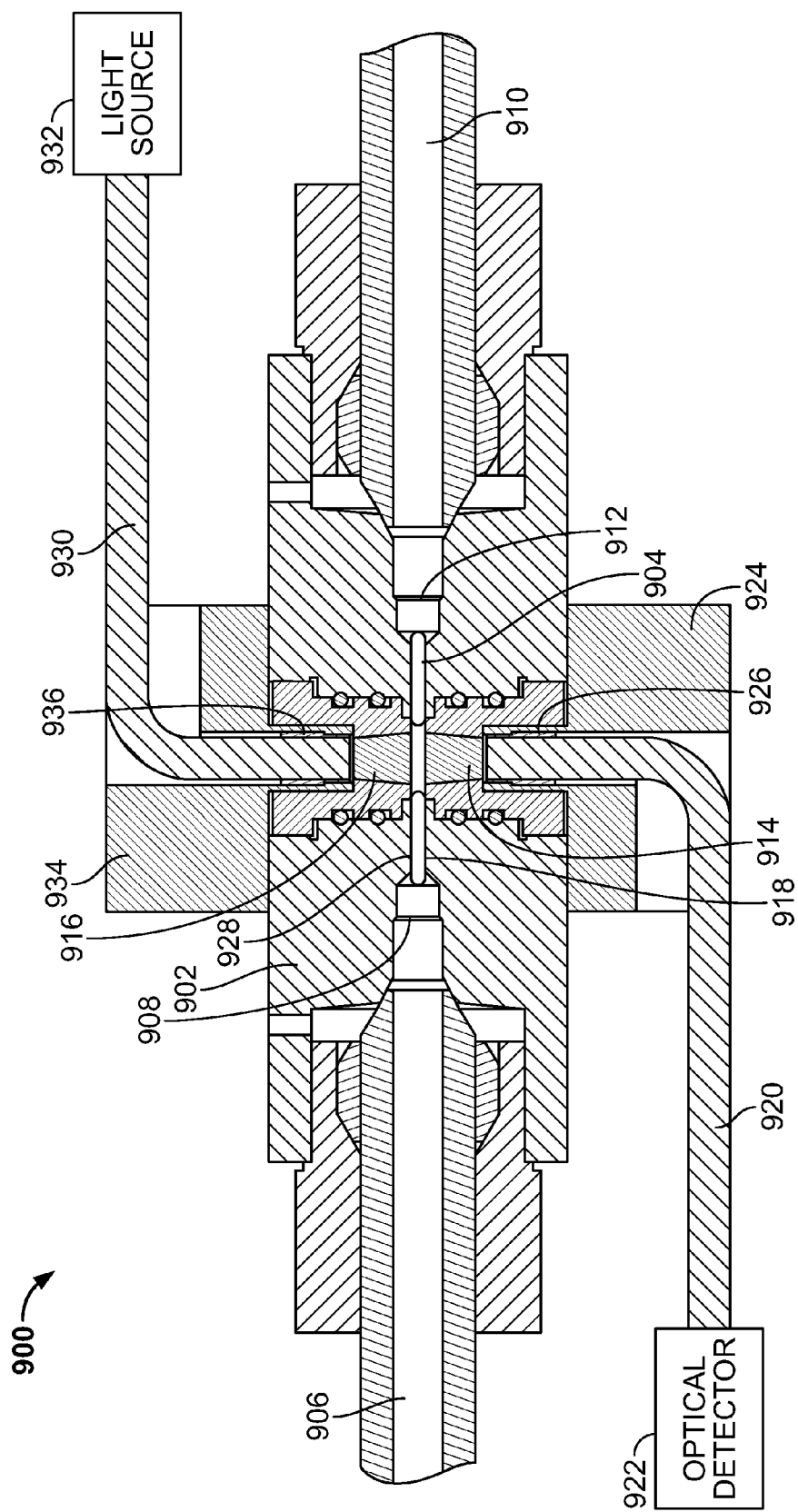
FIG. 9 illustrates yet another example optical window assembly disclosed herein.

FIG. 9 illustrates another example optical window assembly 900 disclosed herein, which may be used to analyze formation fluid flowing in a downhole tool such as, for example, the LWD tool 120 of FIGS. 1-2, the wireline tool 300, and/or any other suitable downhole tool. The example optical window assembly 900 may be used in a variety of downhole applications such as, for example, logging-while-drilling, sampling, production logging, etc. In the illustrated example, the optical window assembly 900 includes a first fixture 902. In some examples, the first fixture 902 is coupled to and/or integral with a chassis of the downhole tool (e.g., a support disposed in the drill string 100). The example first fixture 902 defines a fluid flow passageway 904 in fluid communication with a subterranean formation via a first flowline 906. In the illustrated example, the first flowline 906 is coupled to the first fixture 902 via a first connector or fitting 908. The example fluid flow passageway 904 is also in fluid communication with a second flowline 910. In the illustrated example, the second flowline 910 is coupled to the first fixture 902 via a second connector or fitting 912. The second flowline 910 may direct fluid from the fluid flow passageway 904 to a port (not shown) through which the fluid is expelled (e.g., into the borehole 11). In some examples, the second flowline 910 directs the fluid to one or more fluid collecting chambers (e.g., the fluid collecting chambers 326 and 328 of FIG. 3). In some examples, one or more sensors, valves, gauges, flowlines and/or other devices are in fluid communication with the first flowline 906 and/or the second flowline 910 to direct and/or control fluid flow and/or determine one or more characteristics and/or properties of the fluid.

A first optical window 914 and a second optical window 916 are in optical communication via the fluid flow passageway 904. In the illustrated example, the first optical window 914 is disposed on a first side 918 of the fluid flow passageway 904. A first fiber bundle 920 is operatively coupled to a photodetector or optical detector 922 (e.g., a spectrometer) and the first optical window 914 to define an optical path between the optical detector 922 and the first optical window 914. Other examples may employ different and/or additional devices to define the optical path and/or direct light from the first optical window 914 to the optical detector 922 such as, for example, one or more optics (e.g., lenses, filters, mirrors, etc.). In the illustrated example, the first fiber bundle 920 is directed to the first optical window 914 via a first cap 924. The example first cap 924 defines a first channel 926 to direct the first fiber bundle 920 to the first optical window 914. The first cap 924 may be coupled to the first fixture 902 via, for example, a brazed connection, a weld, an adhesive, etc. In some examples, the first cap 924 is removably coupled to the first fixture 902 via, for example, mechanical fasteners (e.g., bolts) to enable disassembly and/or reassembly of the first cap 924 with the optical window assembly 900 to facilitate maintenance and/or cleaning of the first fiber bundle 920, the first optical window 914, and/or other components of the optical window assembly 900.

The example second optical window 916 is disposed on a second side 928 of the fluid flow passageway 904 opposite the first side 918. Thus, the fluid flow passageway 904 interposes the first optical window 914 and the second optical window 916. A second fiber bundle 930 is optically coupled to a light source 932 (e.g., one or more diode lasers, light emitting diodes (LEDs), etc.) and the second optical window 916 to define an optical path between the light source 932 and the second optical window 916. Other examples may employ different and/or additional devices to define the optical path and/or direct light from the light source 932 to the second optical window 916 such as, for example, one or more optics (e.g., lenses, filters, mirrors, etc.). In the illustrated example, the second fiber bundle 930 is directed to the second optical window 916 via a second cap 934. The example second cap 934 directs the second fiber bundle 930 to the second optical window 916 via a second channel 936. In some examples, the second cap 934 is removably coupled to the first fixture 902 via, for example, mechanical fasteners (e.g., bolts) to enable disassembly and/or reassembly of the second cap 934 with the optical window assembly 900 to facilitate maintenance and/or cleaning of the second fiber bundle 930, the second optical window 916, and/or other components of the example optical window assembly 900.

Figure 10:
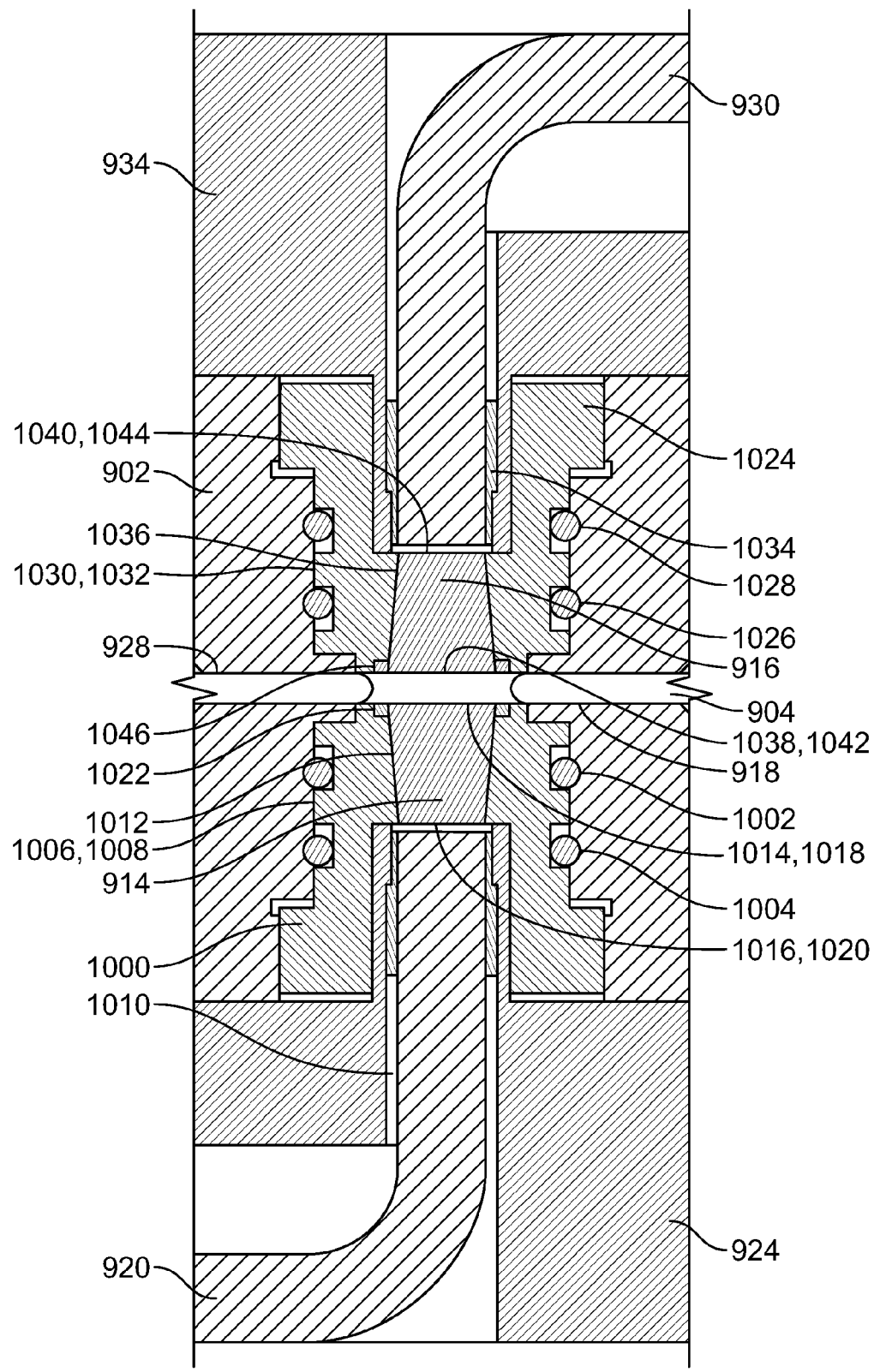
FIG. 10 illustrates a first optical window and a second optical window of the example optical window assembly of FIG. 9

FIG. 10 is an enlarged view of the first optical window 914 and the second optical window 916 of FIG. 9. In the illustrated example, the first optical window 914 is coupled to the first fixture 902 via a second fixture 1000. The example second fixture 1000 is removably coupled to the first fixture 902. In some examples, the second fixture 1000 is removably coupled to the first fixture 902 via one or more fasteners (e.g., bolts) and/or any other suitable technique. In some examples, the second fixture 1000 is also removably coupled to the first cap 924. A first seal 1002 (e.g., an o-ring) and a second seal 1004 (e.g., an o-ring) are disposed between the first fixture 902 and the second fixture 1000 to provide a fluid seal between a surface 1006 of the second fixture 1000 and a surface 1008 of the first fixture 902. The example second fixture 1000 defines a third channel 1010 to direct the first fiber bundle 920 to the first optical window 914.

The example second fixture 1000 of FIG. 10 defines a first space or aperture 1012 in communication with the fluid flow passageway 904 and the third channel 1010 to receive the first optical window 914. In the illustrated example, the first space 1012 has a tapered shape (e.g., frustum-shaped, cone-shaped, etc.) such that a first portion 1014 of the first aperture 1012 adjacent the fluid flow passageway 904 has a first size (e.g., diameter, area, etc.) and a second portion 1016 of the first aperture 1012 adjacent the first fiber bundle 920 has a second size (e.g., diameter, area, etc.) less than the first size.

The example first optical window 914 is disposed in the first aperture 1012. A first end 1018 of the first optical window 914 is adjacent the fluid flow passageway 904. As the fluid flows through the fluid flow passageway 904, the fluid flows across and contacts the first end 1018 of the first optical window 914. A second end 1020 of the first optical window 914 is operatively coupled to the first fiber bundle 920. In the illustrated example, the first optical window 914 has a tapered shape (e.g., frustum-shaped, cone-shaped, etc.) such that a cross-sectional size of the first optical window 914 decreases from the first end 1018 toward the second end 1020 along at least a portion of the first optical window 914. In the illustrated example, the first optical window 914 is substantially composed of sapphire ($Al_2O_3$). In other examples, the first optical window 914 may be composed of sapphire and/or one or more other materials. The example first optical window 914 is rigidly coupled to the second fixture 1000 via a first connection 1022. The example first connection 1022 provides a fluid seal between the first optical window 914 and the second fixture 1000. The first connection 1022 may be a brazed connection similar or substantially identical to the example connection 600 of FIG. 6.

The example second fixture 1000 may be disassembled from the example first fixture 902, the first fiber bundle 920 and/or the first cap 924 to facilitate maintenance and/or cleaning of the example first optical window 911, the fluid flow passageway 904, the first fiber bundle 920, the first cap 924, and/or other components of the optical window assembly 900. For example, the second fixture 1000 may be disassembled from the first fixture 902, the first cap 924 and the first fiber bundle 920 to enable the first end 1018 and the second end 1020 of the first optical window 914 to be cleaned. When the second fixture 100 is disassembled from the first fixture 902, the first end 1042 of the second optical window 916 is accessible via the fluid flow passageway 904 for cleaning, maintenance, etc.

In the illustrated example, the second optical window 916 is coupled to the first fixture 902 via a third fixture 1024. The example third fixture 1024 is removably coupled to the first fixture 902. In some examples, the third fixture 1024 is removably coupled to the first fixture 902 via one or more fasteners (e.g., bolts) and/or any other suitable technique. In some examples, the third fixture 1024 is also removably coupled to the second cap 934. A third seal 1026 (e.g., an o-ring) and a fourth seal 1028 (e.g., an o-ring) are disposed between the first fixture 902 and the third fixture 1024 to provide a fluid seal between a surface 1030 of the third fixture 1024 and a surface 1032 of the first fixture 902. The example third fixture 1024 defines a fourth channel 1034 to direct the second fiber bundle 930 to the second optical window 916.

The example third fixture 1024 of FIG. 10 defines a second space or aperture 1036 in communication with the fluid flow passageway 904 and the fourth channel 1034 to receive the second optical window 916. The second aperture 1036 has a tapered shape (e.g., frustum-shaped, cone-shaped, etc.) such that a first portion 1038 of the second aperture 1036 adjacent the fluid flow passageway 904 has a first size (e.g., diameter, area, etc.) and a second portion 1040 of the second aperture 1036 adjacent the second fiber bundle 930 has a second size (e.g., diameter, area, etc.) less than the first size. The example second optical window 916 is disposed in the second aperture 1036 to enable a first end 1042 of the second optical window 916 to be in contact with the fluid as the fluid flows through the fluid flow passageway 904. The second fiber bundle 930 is operatively coupled to a second end 1044 of the second optical window 916. In the illustrated example, the second optical window 916 has a tapered shape (e.g., frustum-shaped, cone-shaped, etc.) such that a cross-sectional size of the second optical window 916 decreases from the first end 1042 toward the second end 1044 along at least a portion of the second optical window 916. In the illustrated example, the second optical window 916 is substantially composed of sapphire ($Al_2O_3$). In other examples, the second optical window 916 may be composed of sapphire and/or one or more other materials. The second optical window 916 is rigidly coupled to the third fixture 1024 via a second connection 1046. The example second connection 1046 provides a fluid seal between the second optical window 916 and the third fixture 1024. The second connection 1046 of FIG. 10 may be a brazed connection similar or substantially identical to the example connection 600 of FIG. 6.

The example third fixture 1024 may be disassembled from the example first fixture 902, the second fiber bundle 930 and/or the second cap 934 to facilitate maintenance and/or cleaning of the example second optical window 916, the fluid flow passageway 904, the second fiber bundle 930, the second cap 934, and/or other components of the optical window assembly 900. For example, the third fixture 1024 may be disassembled from the first fixture 902, the second cap 934 and the second fiber bundle 930 to enable the first end 1042 and the second end 1044 of the second optical window 916 to be cleaned. When the third fixture 1024 is disassembled from the first fixture 902, the first end 1018 of the first optical window 914 is accessible via the fluid flow passageway 904 for maintenance, cleaning, etc.

Although a few example embodiments have been described in detail above, those skilled in the art will readily appreciate that many modifications are possible in the example embodiments without materially departing from the scope of this disclosure. Accordingly, such modifications are intended to be included within the scope of this disclosure as defined in the following claims. In the claims, means-plus-function clauses are intended to cover the structures described herein as performing the recited function and not just structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

What is claimed is:

1. An apparatus, comprising:
 a first fixture defining a fluid flow passageway;
 a second fixture defining an aperture, the second fixture coupled to the first fixture, the aperture having a tapered shape extending between a first portion of the aperture adjacent the fluid flow passageway and a second portion of the aperture positioned to receive a fiber bundle, the second portion having a smaller cross-sectional size than the first portion;
 a first optical window disposed in the aperture, the first optical window having a first end and a second end, the first end to be in contact with fluid in the fluid flow passageway, wherein a cross-sectional size of the first optical window decreases from the first end toward the second end along at least a portion of the first optical window such that a tapered shape of the first optical window fits the tapered shape of the aperture and thus blocks removal of the first optical window in a direction toward the fiber bundle while enabling force applied to the first optical window via the fluid to be transferred to the first fixture;
 a second optical window in optical communication with the first optical window via the fluid flow passageway; and
 a third fixture defining an aperture to receive the second optical window, the third fixture coupled to the first fixture.

2. The apparatus of claim 1, wherein the second optical window has a third end and a fourth end, the third end to be in contact with the fluid in the fluid flow passageway, a cross-sectional size of the second optical window decreasing from the third end toward the fourth end along at least a portion of the second optical window.

3. The apparatus of claim 1, further comprising a fiber bundle operatively coupled to the first optical window, wherein substantially no force associated with fluid pressure in the fluid flow passageway is to be applied to the fiber bundle.

4. The apparatus of claim 1, wherein at least a portion of the first optical window is composed of sapphire.

5. The apparatus of claim 1, wherein the second fixture is coupled to the first fixture via a weld.

6. The apparatus of claim 1, wherein the second fixture is removably coupled to the first fixture.

7. An apparatus, comprising:
a plurality of fixtures coupled together to define an optical window assembly;
a first fixture of the plurality of fixtures defining a fluid flow passageway, a second fixture of the plurality of fixtures defining a first frustum-shaped space extending between the fluid flow passageway of the first fixture and a fiber bundle opening, the first frustum-shaped space having a larger diameter proximate the fluid flow passageway;
a first optical window, at least a portion of the first optical window being frustum-shaped and generally matching the first frustum-shaped space, the first optical window being disposed in the first frustum-shaped space such that the frustum-shape of the first optical window enables force applied to the first optical window via the fluid to be transferred to the second fixture;
a third fixture of the plurality of fixtures coupled to the first fixture and a second optical window disposed in the third fixture
wherein the second fixture is coupled to the first fixture and a third fixture coupled to the second fixture and a second optical window disposed in the third fixture.

8. The apparatus of claim 7, wherein the first optical window is brazed to the second fixture of the plurality of fixtures.

9. The apparatus of claim 7, wherein the first fixture is welded to the second fixture of the plurality of fixtures.

10. The apparatus of claim 7, wherein the first fixture is removably coupled to the second fixture.

11. The apparatus of claim 10 further comprising a second optical window in optical communication with the first optical window via the fluid flow passageway.

12. An apparatus, comprising:
a first optical window to be in communication with a fluid flow passageway, the first optical window including a tapered portion;
a first fixture defining a space to receive the tapered portion of the first optical window from the side of the first fixture proximate the fluid flow passageway such that the tapered portion of the first optical window enables force applied to the first optical window via the fluid to be transferred to the first fixture, wherein the first optical window is to be fused to the first fixture;
a second fixture defining the fluid flow passageway, the first fixture coupled to the second fixture; and
a fiber bundle directed to the first optical window by a cap coupled to the first fixture, the shape of the space to receive the tapered portion of the first optical window preventing removal of the first optical window toward the fiber bundle;
a second optical window in optical communication with the first optical window via the fluid flow passageway of the second fixture; and
a third fixture defining an aperture to receive the second optical window, the third fixture coupled to the first fixture.

13. The apparatus of claim 12, wherein the first optical window is fused to the fixture via a brazed connection.

14. The apparatus of claim 12, wherein the first fixture is removably coupled to the second fixture.

15. The apparatus of claim 12, wherein the first fixture is welded to the second fixture.

* * * * *